United States Patent [19]

Pryor et al.

[11] 4,002,042
[45] Jan. 11, 1977

[54] RECOVERY OF $C_2+$ HYDROCARBONS BY PLURAL STAGE RECTIFICATION AND FIRST STAGE DEPHLEGMATION

[75] Inventors: John A. Pryor, Emmaus; Howard C. Rowles, Center Valley, both of Pa.

[73] Assignee: Air Products and Chemicals, Inc., Allentown, Pa.

[22] Filed: Nov. 27, 1974

[21] Appl. No.: 527,516

[52] U.S. Cl. .................................. 62/28; 62/31; 62/40

[51] Int. Cl.² .................................. F25J 3/02

[58] Field of Search ............. 62/9, 11, 23, 24, 25, 62/26, 27, 28, 29, 30, 31, 32, 34, 36, 38, 39, 41, 42, 43

[56] References Cited
UNITED STATES PATENTS

| | | | |
|---|---|---|---|
| 2,582,068 | 1/1952 | Roberts | 62/25 |
| 2,880,592 | 4/1959 | Davison et al. | 62/28 |
| 3,186,182 | 6/1965 | Grossmann et al. | 62/28 |
| 3,276,212 | 10/1966 | Ichihara | 62/26 |
| 3,359,743 | 12/1967 | DiNapoli | 62/28 |
| 3,675,435 | 7/1972 | Jackson et al. | 62/23 |

OTHER PUBLICATIONS

Hackh's Chemical Dictionary; 4th Edition; Grant; McGraw-Hill; 1969; p. 203.

Primary Examiner—Frank W. Lutter
Assistant Examiner—Frank Sever
Attorney, Agent, or Firm—Bernard M. Weiss; Barry Moyerman

[57] ABSTRACT

A process is provided for the separation and recovery of a major portion of the $C_2+$ hydrocarbon content of a feed gas comprising hydrogen, methane, ethylene, and ethane. The feed gas is introduced to a dephlegmator to effect its separation into a vapor stream and a condensate stream. The condensate stream which is rich in $C_2+$ hydrocarbons is passed to a demethanizer column where it is fractionated into an overhead methane-hydrogen stream and a bottoms product ethylene-ethane+ stream.

19 Claims, 2 Drawing Figures

RECOVERY OF $C_2+$ HYDROCARBONS BY PLURAL STAGE RECTIFICATION AND FIRST STAGE DEPHLEGMATION

BACKGROUND OF THE INVENTION

1. Field of the Invention

This invention relates to a low temperature process for separation of a gaseous mixture into fractions. A gaseous mixture containing components of different boiling points, all of which are below 32° F at atmospheric pressure, is passed through a sequence of partial liquefaction, rectification, and separation steps, characterized by high thermal efficiency and low power requirements, to effect separation of the mixture into streams enriched with their respective components.

2. Description of the Prior Art

Numerous methods are known in the prior art involving the separation of gases. A particular method for the separation of ethylene from a gaseous stream comprising carbon dioxide, hydrogen, and low-boiling hydrocarbons is given in U.S. Pat. No. 3,729,944. The method utilizes an expanded tail gas and its equilibrium liquid as refrigerants.

Dephlegmators themselves are not new to the art. U.S. Pat. No. 2,582,068 describes an arrangement applicable to the separation of binary mixtures, whereby three dephlegmators are charged with a feed gas in parallel and the vapors discharged from their overhead are combined and sent to one or more additional dephlegmators in series.

The prior art process is particularly directed to separating a binary mixture that is available at a high initial pressure when it is desired to recover the more volatile component at substantially that initial pressure. The less volatile component is expanded to about atmospheric pressure to supply refrigeration to make up for heat leakage and other thermodynamic losses. This method is said to be especially useful for separating hydrogen and methane, since these two components have widely separated boiling points.

SUMMARY OF THE INVENTION

This invention provides a method of separating and recovering a major portion of the $C_2+$ hydrocarbon content of a feed gas comprising hydrogen, methane, ethylene and ethane which comprises:

a. introducing the feed gas into a dephlegmation zone;

b. cooling the feed gas in the dephlegmation zone by indirect heat exchange to form a condensate stream containing the major portion of the $C_2+$ hydrocarbons in the feed gas and a vapor stream containing the balance of the uncondensed material from the feed gas;

c. withdrawing the vapor stream from the dephlegmation zone;

d. passing the condensate stream from the dephlegmation zone to a rectification zone; and e. withdrawing from the rectification zone a $C_1$ and lighter stream (streams of this type contain $C_1$ and lighter components such as hydrogen) and a $C_2+$ hydrocarbon stream, whereby the energy requirements for the refrigeration utilized in separating the $C_2+$ hydrocarbons from the $C_1$ and lighter components are reduced.

The dephlegmation zone consists essentially of a plurality of the indirect heat exchange passages through which the feed gas stream, which may be of a type obtained from the cracking of naphtha, light oil, or an ethane gas stream, is passed in an upward direction. Refrigerant means is provided in indirect heat exchange with these passages. Thus, as the feed gas flows upward, some of the mixture condenses on the walls of the passages forming a reflux liquid. Accordingly, interaction takes place between the upward flowing gas stream and the stream of cooler liquid flowing downward. This liquid stream gradually becomes enriched with the less volatile components of the feed gas, i.e., ethylene and ethane, as it flows downward.

The specific operating conditions for the dephlegmation zone will vary as a function of the pressure and composition at which the feed gas is supplied, the indirect heat exchange capacity provided and the properties and quantity of the refrigerant utilized.

BRIEF DESCRIPTION OF THE DRAWINGS

FIG. 2 is a schematic flow diagram for another embodiment of the invention.

DESCRIPTION OF THE PREFERRED EMBODIMENTS

Figure 1:
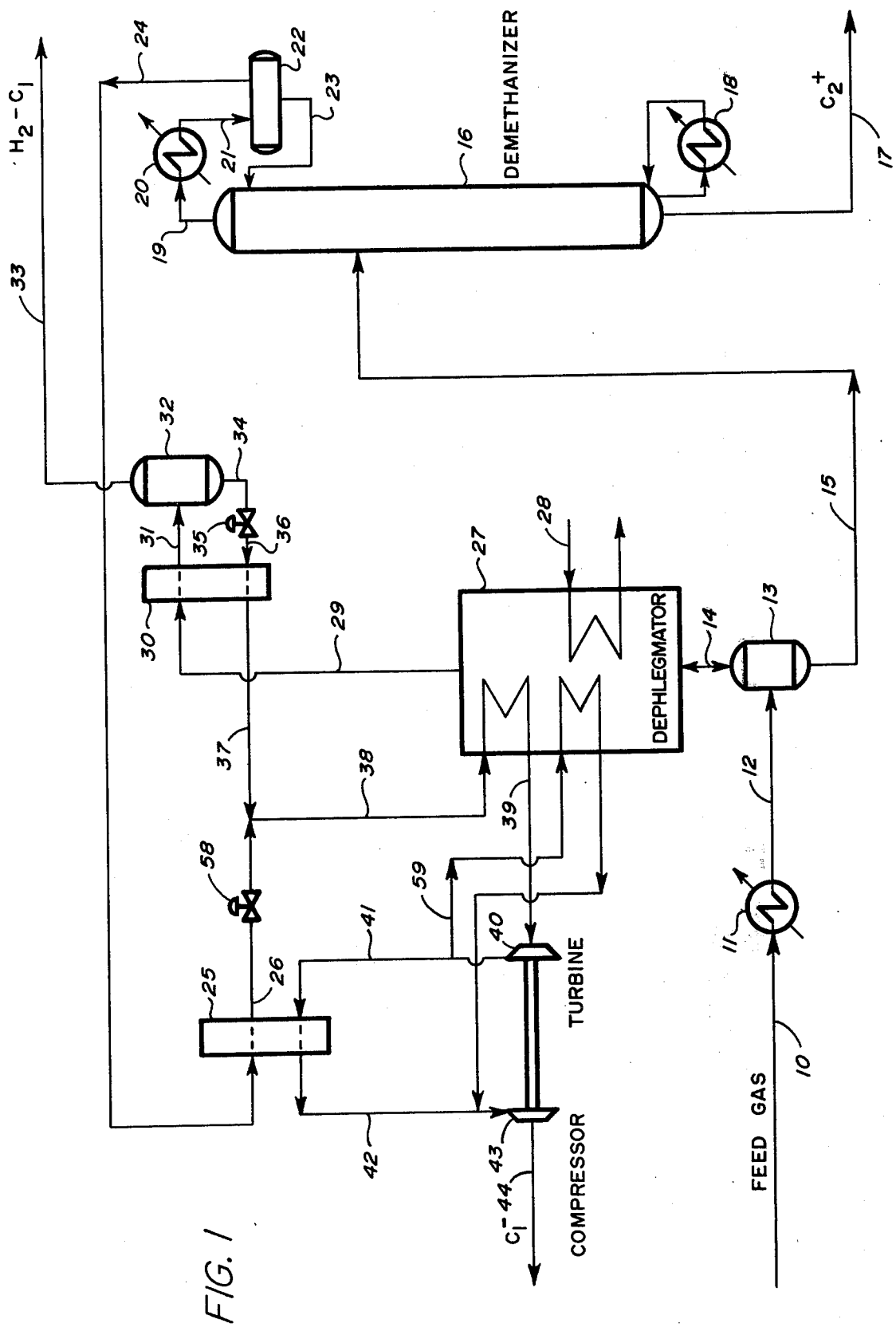
FIG. 1 is a schematic flow diagram of a separation and recovery system according to one embodiment of the invention.

Referring now to FIG. 1, a gaseous feedstream enters the system through line 10 at a pressure of about 500 p.s.i.a. and a temperature of about $-32°$ F and has the approximate composition:

|  | Mole Percent |
| --- | --- |
| Hydrogen | 17.87 |
| Methane | 35.10 |
| Ethylene | 35.70 |
| Ethane | 11.27 |
| Propylene+ | .06 |
|  | 100.00 |

This feed gas mixture is pretreated by being cooled and partially condensed in heat exchanger 11 and introduced to separator 13 via line 12. A vapor is withdrawn from separator 13 and is passed through line 14 and introduced into dephlegmator 27 at a temperature of about $-76°$ F.

The vapor flows in an upward direction in dephlegmator 27 through a plurality of indirect heat exchange passages not shown. An extraneous refrigerant such as ethylene is evaporated to cool the lower section of the heat exchange passages and is shown schematically as passing through cooling coil 28. A mixed stream of hydrogen and methane to be defined later is warmed and evaporated to cool the upper section. As the vapor is cooled, some of the mixture condenses on the walls of the passages forming a reflux liquid that flows in a downward direction. Accordingly, interaction takes place between the stream of gas flowing upwards and the stream of cold liquid flowing downwards. Rectification results whereby the gaseous mixture leaving the dephlegmator becomes enriched in $C_1$ and lighter components and the liquid leaving is enriched in $C_2+$ hydrocarbon components.

The liquid stream produced in the dephlegmator is withdrawn at a temperature near, but ordinarily lower than the vapor inlet temperature and passed downwardly through line 14 to separator 13. Line 14 is the same line through which vapor is flowing upward from separator 13, as previously discussed. Dual flows, such as these, are connoted by the double arrows shown in FIGS. 1 and 2. There it is mixed with the condensate produced in heat exchanger 11 and the admixed liquid stream is fed through line 15 to the demethanizer 16 at about 492 p.s.i.a. and −80° F.

If desired, one or more additional liquid streams may be formed during pretreatment of the feed gas, which is not herein shown, and fed to demethanizer 16. These liquid streams might be formed by cooling the feed gas to about −32° F in a series of steps, whereby partial condensing is effected in at least one of the steps. Liquid streams thus formed would tend to be richer in higher boiling components than the admixed liquid stream fed to the demethanizer via line 15. They are treated in demethanizer 16 to facilitate recovery of their $C_1$ and lighter components.

In the demethanizer, an overhead vapor fraction, primarily consisting of methane and hydrogen, is withdrawn through line 19, is cooled and partially condensed in heat exchanger 20, and through line 21 is introduced into separator 22, where the liquid fraction is removed and returned as reflux through line 23 to demethanizer 16. The vapor fraction from separator 22 is withdrawn through line 24 and cooled and partially condensed in heat exchanger 25.

Heat is supplied to reboil the demethanizer in heat exchanger 18. A liquid demethanizer bottom product having the approximate composition of

|  | Mole Percent |
|---|---|
| Methane | .01 |
| Ethylene | 75.78 |
| Ethane | 24.08 |
| Propylene+ | .13 |
|  | 100.00 | is withdrawn at about 475 p.s.i.a. and 25° F via line 17 and recovered.

A gaseous mixture of the approximate composition

|  | Mole Percent |
|---|---|
| Hydrogen | 45.68 |
| Methane | 54.10 |
| Ethylene | .22 |
|  | 100.00 | is withdrawn from the dephlegmator at about 495 p.s.i.a. and −173° F. It is passed through line 29 and is cooled in heat exchanger 30 to about −193° F and partially condensed, and introduced via line 31 into phase separator 32.

A vapor stream of approximate composition

|  | Mole Percent |
|---|---|
| Hydrogen | 62.10 |
| Methane | 37.87 |
| Ethylene | .03 |
|  | 100.00 | is withdrawn from phase separator 32 and recovered via line 33. This vapor stream, if desired, could be further separated into its main components of hydrogen and methane. It could also be used in indirect heat exchanger with other streams to provide cooling for them.

The liquid fraction separated in phase separator 32 is withdrawn and passed through line 34 to expansion valve 35 to be expanded from a pressure of 485 p.s.i.a. to a pressure of 325 p.s.i.a. and a temperature of about −195° F. It is then passed through line 36 to heat exchanger 30 where it is warmed in indirect heat exchange with the overhead gaseous mixture from the dephlegmator and is then passed through line 37 and admixed with the partially condensed stream withdrawn from heat exchanger 25 via line 26 and expansion valve 58. The stream which is passed through expansion valve 58 is expanded from a pressure of 460 p.s.i.a. to a pressure of 320 p.s.i.a. and a temperature of −176° F. The admixed stream is then introduced through line 38 to the dephlegmator 27 to cool by evaporation the upper section of heat exchange passages.

This stream is withdrawn as all vapor from the dephlegmator at about 315 p.s.i.a. and −152° F and is passed through line 39 to be expanded to about 65 p.s.i.a. and −198° F in turbine 40. The expanded gas from turbine 40 is passed through line 41 to be warmed to about −144° F by indirect heat exchange with the overhead vapor fraction from separator 22 in heat exchanger 25. It is then conducted through line 42 to compressor 43 where its pressure is increased to about 85 p.s.i.a. Instead of passing all of the expanded gas from turbine 40 through heat exchanger 25, at least a portion of this gas properly controlled and directed, may be introduced into dephlegmator 27 via line 59 to be utilized in the indirect heat exchange occurring therein and then passed to compressor 43.

The turbine 40 and compressor 43 are both mounted on a common shaft. This enables power extracted from the stream expanding through the turbine 40 to be used to drive the compressor 43. Alternatively, the turbine could be connected to the compressor by means of a gear box in order to separately optimize the speeds of the compressor and turbine wheels. Also, more than one turbine may be mounted in seriatim with one or more compressors. This mounting arrangement applies when common shaft mountings as well as gear box mountings are concerned.

The vapor discharged from the compressor is passed through line 44 and recovered. Its composition is about

|  | Mole Percent |
|---|---|
| Hydrogen | 4.75 |
| Methane | 94.65 |
| Ethylene | .60 |
|  | 100.00 |

Figure 2:
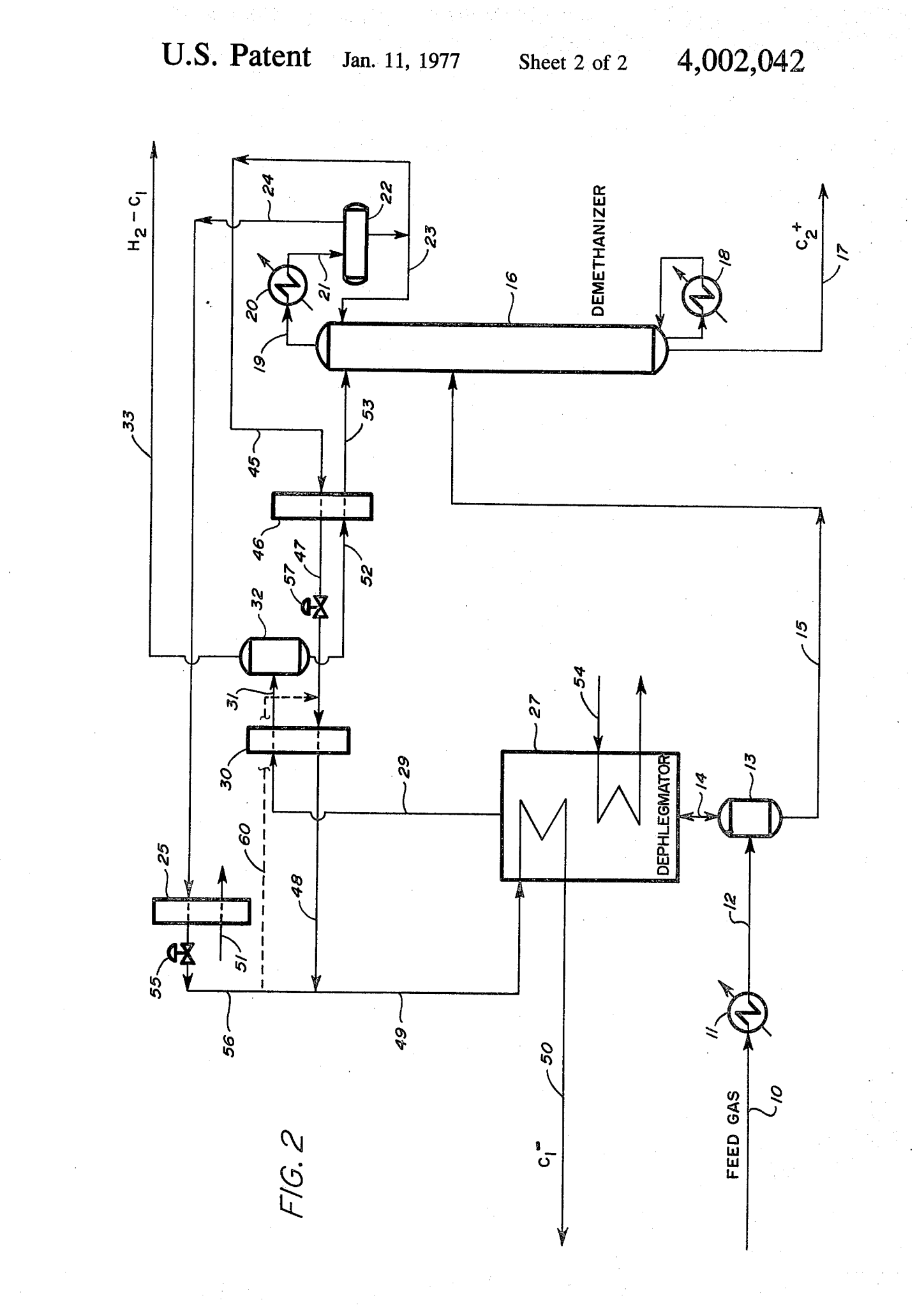

The following is a specific example of operation with respect to the embodiment shown in FIG. 2. A feed gas mixture of composition

|  | Mole Percent |
|---|---|
| Hydrogen | 26.50 |
| Carbon Monoxide | .15 |
| Methane | 37.90 |
| Ethylene | 26.30 |
| Ethane | 7.18 |
| Propylene+ | 1.97 |
|  | 100.00 | enters the system through line 10 at a pressure of about 516 p.s.i.a. and a temperature of −35° F. This gaseous mixture is pretreated by being cooled and partially condensed in heat exchanger 11 and introduced to separator 13 via line 12.

A vapor of composition

|  | Mole Percent |
|---|---|
| Hydrogen | 31.82 |
| Carbon Monoxide | .18 |
| Methane | 41.94 |
| Ethylene | 20.70 |
| Ethane | 4.81 |
| Propylene+ | .55 |
|  | 100.00 | is withdrawn from separator 13, passed through line 14 and introduced into dephlegmator 27 at a temperature of about −62° F.

The vapor flows in an upward direction in dephlegmator 27 through a plurality of indirect heat exchange passages which are not shown. An extraneous refrigerant such as ethylene is evaporated in the lower section of the heat exchange passages to provide cooling and is shown schematically as passing through cooling coil 54. A mixed stream consisting essentially of hydrogen and methane, to be defined later, is warmed and evaporated to cool an upper section of the dephlegmator.

As the vapor is cooled in the dephlegmator, part of the mixture condenses and flows in a downward direction. Rectification takes place between the upward flowing vapor and the downward flowing condensate, whereby a gaseous mixture is produced which is enriched in $C_1$ and lighter components and a condensate is produced which is enriched in $C_2+$ hydrocarbon components.

The condensate is withdrawn from the dephlegmator at a temperature near, but ordinarily lower than the vapor inlet temperature and passed downwardly through line 14 to separator 13. In separator 13 the condensate from the dephlegmator is admixed with the condensate produced in heat exchanger 11 and the admixed liquid stream is fed to the demethanizer 16 via line 15 at about 514 p.s.i.a. and −72° F. Additional liquid streams formed during pretreatment of the feed gas, not herein shown, by cooling the gas to about −35° F in a series of steps and partially condensing in at least some of these steps, may also be fed to demethanizer 16. These liquid streams would be correspondingly richer in higher boiling components than the admixed liquid stream fed to the demethanizer mentioned above. The reason for feeding these additional liquid streams to the demethanizer is to recover their $C_1$ and lighter components.

A gaseous mixture of approximate composition

|  | Mole Percent |
|---|---|
| Hydrogen | 47.34 |
| Carbon Monoxide | .26 |
| Methane | 51.70 |
| Ethylene | .70 |
|  | 100.00 | is withdrawn from the dephlegmator at about 514 p.s.i.a. and its dew point of −169° F. It is passed through line 29 and is cooled to about −210° F and partially condensed in heat exchanger 30, and then introduced via line 31 into phase separator 32.

A vapor stream of approximate composition

|  | Mole Percent |
|---|---|
| Hydrogen | 75.78 |
| Carbon Monoxide | .29 |
| Methane | 23.90 |
| Ethylene | .03 |
|  | 100.00 | is withdrawn from phase separator 32 and recovered via line 33. If desired, this vapor stream could be separated further into its hydrogen and methane components and could also be used to provide cooling to other streams by way of indirect heat exchange.

The liquid fraction separated in phase separator 32 is withdrawn and passed through line 52 to heat exchanger 46, where it is warmed to about −153° F and partially vaporized. In this condition it is introduced as a feed to the enriching section of the demethanizer 16 via line 53.

A liquid bottom product having the approximate composition

|  | Mole Percent |
|---|---|
| Methane | .04 |
| Ethylene | 74.10 |
| Ethane | 20.29 |
| Propylene+ | 5.57 |
|  | 100.00 | is withdrawn from the demethanizer at about 475 p.s.i.a. and 30° F via line 17 and is recovered. This product stream contains the major portion of the $C_2+$ hydrocarbon content of the feed streams.

Heat is supplied to reboil the demethanizer in heat exchanger 18. An overhead vapor fraction, consisting mostly of methane and hydrogen, is withdrawn from the demethanizer through line 19, cooled to about −148° F and partially condensed in heat exchanger 20, and is passed through line 21 and introduced into separator 22. A liquid stream is withdrawn from separator 22 and divided into streams. One of these liquid streams is returned as reflux through line 23 to demethanizer 16. The other liquid stream is passed through line 45, cooled to about −197° F in heat exchanger 46 against the liquid fraction withdrawn from phase separator 32, passed through line 47 to expansion valve 57, expanded to about 104 p.s.i.a. and −210° F and heated and partially vaporized in heat exchanger 30 against the gaseous mixture withdrawn from the dephlegmator to provide a refrigerant stream.

A vapor stream is withdrawn from separator 22, passed through line 24, cooled to about −157° F and partially condensed in heat exchanger 25, and expanded through valve 55 to about 100 p.s.i.a. and −210° F to provide a second refrigerant. An extraneous coolant stream, shown passing through line 51, is used to cool heat exchanger 25.

The refrigerant stream withdrawn from heat exchanger 30 is passed through line 48 and is admixed with the second refrigerant leaving expansion valve 55 via line 56 to provide a combined refrigerant stream. This combined refrigerant stream is passed through line 49 and is introduced to the upper section of indirect heat exchange passages of dephlegmator 27 where it is warmed and evaporated to provide cooling. This stream is then withdrawn as an all vapor stream from the dephlegmator and conducted through line 50 to be recovered. Its composition is

|  | Mole Percent |
|---|---|
| Hydrogen | 4.58 |
| Carbon Monoxide | .18 |
| Methane | 95.13 |
| Ethylene | .11 |
|  | 100.00 |

Alternately, the liquid stream cooled in heat exchanger 46 and expanded through valve 57 can be admixed with the second refrigerant leaving expansion valve 55 prior to introduction into heat exchanger 30. The second refrigerant would be passed through line 56 and then dotted line 60 after leaving expansion valve 55. The admixed refrigerant stream is then heated and partially evaporated in heat exchanger 30 and passed through lines 48 and 49 and introduced into dephlegmator 27 to be utilized in the indirect heat exchange taking place therein. This alternate scheme could provide an especially efficient heat transfer in heat exchanger 30.

We claim:
1. A method of separating and recovering a major portion of the $C_2+$ hydrocarbon content of a feed gas comprising hydrogen, methane, ethylene and ethane, which comprises:
    a. introducing said feed gas into a dephlegmation zone comprising a plurality of indirect heat exchange passages through which at least a portion of the feed gas passes in an upward direction and is cooled by refrigerant means provided in indirect heat exchange with said passages, as said gas flows upward it partially condenses on the walls of said passages forming a reflux liquid such that interaction takes place between the upward flowing gas stream and the stream of cooler liquid flowing downward and said liquid gradually becomes enriched with the $C_2+$ hydrocarbons of the feed gas;
    b. cooling at least a portion of said feed gas in the dephlegmation zone by indirect heat exchange to form a condensate stream containing the major portion of the $C_2+$ hydrocarbons in the feed gas and a vapor stream containing the balance of the uncondensed material from the feed gas;
    c. withdrawing the vapor stream from the dephlegmation zone;
    d. passing the condensate stream from the dephlegmation zone to a rectification zone; and
    e. withdrawing from the rectification zone a substantially $C_1$ and lighter stream and a $C_2+$ hydrocarbon stream,
whereby the energy requirements for the refrigeration utilized in separating the $C_2+$ hydrocarbons from the $C_1$ and lighter components are low.

2. The method in accordance with claim 1, wherein the vapor stream of step (c) is at least partially condensed and utilized in the indirect heat exchange occurring in the dephlegmation zone.

3. The method in accordance with claim 2, wherein the condensed portion of the vapor stream is separated from the uncondensed portion and said condensed portion is expanded, partly evaporated, warmed in indirect heat exchange to effect the partial condensation of the vapor stream from the dephlegmation zone, thereby becoming a first dephlegmation zone refrigerant stream and is then utilized in the indirect heat exchange occurring in the dephlegmation zone.

4. The method in accordance with claim 3, wherein the $C_1$ and lighter stream is withdrawn from the rectification zone as a vapor and is then at least partially condensed and admixed with the first dephlegmation zone refrigerant stream and said admixed stream is then utilized in the indirect heat exchange occurring in the dephlegmation zone.

5. The method in accordance with claim 4, wherein said admixed stream is passed from the dephlegmation zone seriatim through at least one turbine and at least one compressor, said turbine and compressor being interconnected whereby energy extracted from the admixed stream as it expands in the turbine is used to drive the compressor, and refrigeration provided by the turbine expansion is utilized to at least partially condense the substantially $C_1$ and lighter vapor stream withdrawn from the rectification zone.

6. The method in accordance with claim 5, wherein the feed gas is partially condensed prior to being introduced to the dephlegmation zone and separated into a first vapor stream which is fed to the dephlegmation zone and a second condensate stream which is admixed with the condensate stream withdrawn from the dephlegmation zone, said admixed condensate stream serving as a feed to the rectification zone.

7. The method in accordance with claim 4, wherein the refrigeration provided by the turbine expansion is utilized in the indirect heat exchange occurring in the dephlegmation zone.

8. The method in accordance with claim 7, wherein the feed gas is partially condensed prior to being introduced to the dephlegmation zone and separated into a first vapor stream which is fed to the dephlegmation zone and a second condensate stream which is admixed with the condensate stream withdrawn from the dephlegmation zone, said admixed condensate stream serving as a feed to the rectification zone.

9. The method in accordance with claim 4, wherein at least a portion of the refrigeration provided by the turbine expansion is utilized to at least partially condense the substantially $C_1$ and lighter vapor stream withdrawn from the rectification zone and the remaining portion of the refrigeration is utilized in the indirect heat exchange occurring in the dephlegmation zone.

10. The method in accordance with claim 9, wherein the feed gas is partially condensed prior to being introduced to the dephlegmation zone and separated into a first vapor stream which is fed to the dephlegmation zone and a second condensate stream which is admixed with the condensate stream withdrawn from the dephlegmation zone, said admixed condensate stream serving as a feed to the rectification zone.

11. The method in accordance with claim 1, wherein the $C_1$ and lighter stream is withdrawn from the rectification zone as a vapor and is then at least partially condensed and utilized in the indirect heat exchange occurring in the dephlegmation zone.

12. The method in accordance with claim 1, wherein the feed gas is partially condensed prior to being introduced to the dephlegmation zone and separated into a first vapor stream which is fed to the dephlegmation zone and a second condensate stream which is fed to the rectification zone.

13. The method in accordance with claim 1, wherein the vapor stream of step (c) is at least partially condensed, separated into a third vapor and a third condensate, and the third condensate is introduced to the rectification zone.

14. The method in accordance with claim 13, wherein the substantially $C_1$ and lighter stream is withdrawn from the rectification zone as a vapor and is at least partially condensed and expanded to form a second refrigerant, and a substantially $C_1$ substantially and lighter liquid stream is withdrawn from the rectification zone and is expanded, partly evaporated, warmed in indirect heat exchange while being utilized in the partial condensation of the vapor stream from the dephlegmation zone, and is then admixed with said second refrigerant to form a combined refrigerant stream which is utilized in the indirect heat exchange occurring in the dephlegmation zone and then recovered.

15. The method in accordance with claim 14, wherein prior to the expansion of the substantially $C_1$ and lighter liquid stream withdrawn from the rectification zone it is cooled in indirect heat exchange with the third condensate, said third condensate being warmed prior to being introduced to the rectification zone.

16. The method in accordance with claim 15, wherein the feed gas is partially condensed prior to being introduced to the dephlegmation zone and separated into a first vapor stream which is fed to the dephlegmation zone and a second condensate stream which is fed to the rectification zone.

17. The method in accordance with claim 13, wherein the substantially $C_1$ and lighter stream is withdrawn from the rectification zone as a vapor and is at least partially condensed and expanded to form a second refrigerant, and a substantially $C_1$ and lighter liquid stream is withdrawn from the rectification zone and is expanded and partly evaporated and then admixed with said second refrigerant to form a mixed refrigerant stream which is warmed in indirect heat exchange while being utilized in the partial condensation of the vapor stream from the dephlegmation zone, and is then utilized in the indirect heat exchange occurring in the dephlegmation zone and then recovered.

18. The method in accordance with claim 17, wherein prior to the expansion of the substantially $C_1$ and lighter liquid stream withdrawn from the rectification zone it is cooled in indirect heat exchange with the third condensate, said third condensate being warmed prior to being introduced to the rectification zone.

19. The method in accordance with claim 18, wherein the feed gas is partially condensed prior to being introduced to the dephlegmation zone and separated into a first vapor stream which is fed to the dephlegmation zone and a second condensate stream which is fed to the rectification zone.

* * * * *